United States Patent
Simonson et al.

(10) Patent No.: US 11,083,593 B1
(45) Date of Patent: Aug. 10, 2021

(54) METHOD AND IMPLANT FOR CONVERTING A TRANSCORPOREAL CORPECTOMY PROCEDURE TO AN INTERVERTEBRAL DISCECTOMY WITH FUSION PROCEDURE

(71) Applicants: Robert E. Simonson, Boca Raton, FL (US); David P. Sachs, Boca Raton, FL (US)

(72) Inventors: Robert E. Simonson, Boca Raton, FL (US); David P. Sachs, Boca Raton, FL (US)

( * ) Notice: Subject to any disclaimer, the term of this patent is extended or adjusted under 35 U.S.C. 154(b) by 0 days.

(21) Appl. No.: 17/139,397

(22) Filed: Dec. 31, 2020

(51) Int. Cl.
*A61F 2/44* (2006.01)
*A61B 17/70* (2006.01)
*A61F 2/30* (2006.01)

(52) U.S. Cl.
CPC ........ *A61F 2/4455* (2013.01); *A61B 17/7059* (2013.01); *A61F 2/30749* (2013.01); *A61F 2002/30181* (2013.01)

(58) Field of Classification Search
CPC .......... A61F 2/44; A61F 2/4455; A61F 2/447; A61F 2/46; A61F 2/4601; A61F 2/4611; A61B 17/7059
See application file for complete search history.

(56) References Cited

U.S. PATENT DOCUMENTS

| | | | | |
|---|---|---|---|---|
| 5,591,235 A * | 1/1997 | Kuslich | ............. | A61B 17/7076 606/261 |
| 7,303,565 B2 * | 12/2007 | Buttermann | ....... | A61B 17/1604 606/86 R |
| 7,803,188 B2 * | 9/2010 | Justis | ................. | A61B 17/7095 623/17.11 |
| 7,867,263 B2 * | 1/2011 | Lowry | ............... | A61B 17/8028 606/281 |
| 7,905,885 B2 * | 3/2011 | Johnson | ................ | A61F 2/4425 606/90 |
| 8,163,021 B2 * | 4/2012 | Lowry | .................. | A61F 2/4611 623/17.11 |
| 8,425,569 B2 * | 4/2013 | O'Farrell | ........... | A61B 17/7059 606/279 |

(Continued)

OTHER PUBLICATIONS

Brochure—Medtronic Sofamor Danek—"Atlantist™ Anterior Cervical Plate System Surgical Technique" by Volker K. H. Sonntag, M.D., Barrow Neurological Institute, Regis W. Haid, Jr., M.D., Emory Clinic, Stephen M. Papadopoulos, Barrow Neurological Institute, M.D.

(Continued)

*Primary Examiner* — Eric S Gibson
(74) *Attorney, Agent, or Firm* — Burr & Forman LLP; Jeffrey H. Kamenetsky

(57) ABSTRACT

A method of performing an anterior cervical fusion procedure is provided. The method includes creating a void in a first vertebral body of a cervical vertebra, the void beginning anteriorly and directed posteriorly creating an exit at a posterior aspect of the vertebral body, after the creation of the void in the first vertebral body, removing at least a portion of a cervical intervertebral disc, the disc located between and adjacent to the first vertebral body and a second vertebral body, and performing a fusion procedure between the first vertebral body and the second vertebral body.

4 Claims, 9 Drawing Sheets

(56) References Cited

U.S. PATENT DOCUMENTS

| | | | |
|---|---|---|---|
| 9,044,338 B2* | 6/2015 | Schaller | A61F 2/442 |
| 10,064,735 B1* | 9/2018 | Simonson | A61F 2/44 |
| 10,751,192 B1* | 8/2020 | Simonson | A61F 2/447 |
| 2005/0277921 A1* | 12/2005 | Eisermann | A61F 2/4405 |
| | | | 623/17.16 |
| 2006/0122704 A1* | 6/2006 | Vresilovic | A61F 2/4611 |
| | | | 623/17.16 |
| 2007/0270851 A1* | 11/2007 | Erickson | A61B 17/8042 |
| | | | 623/17.16 |
| 2009/0076555 A1* | 3/2009 | Lowry | A61B 17/70 |
| | | | 606/280 |
| 2009/0143716 A1* | 6/2009 | Lowry | A61F 2/442 |
| | | | 604/22 |
| 2010/0152793 A1* | 6/2010 | Lowry | A61B 17/88 |
| | | | 606/86 R |
| 2012/0209387 A1* | 8/2012 | Lowry | A61B 17/1757 |
| | | | 623/17.16 |
| 2019/0290445 A1* | 9/2019 | Lowry | A61B 17/1671 |

OTHER PUBLICATIONS

510(k) premarket notification of intent to market and device description of Skyline® Anterior Cervical Plate System, Uniplate® Anterior Cervical Plate System, and Uniplate® 2 Anterior Cervical Plate System, Jul. 25, 2013, Submitted by Medos International Sàrl, Switzerland, DePuy Spine, Inc., Raynham, Massachusetts and Kirsten Lehmuller, Raynham, Massachusetts.

Surgical Technique & Ordering Information, Anterior Cervical Plate System for the Skyline ACP System Description, DePuy Spine Inc., a Johnson & Johnson company, designing surgeons Curtis A. Dickman, MD, Barrow Neurological Institute, Jeffrey S. Fischgrund, MD, William Beaumont Hospital, Michael G. Fehlings, MD, Ph.D., FRCSC, University of Toronto, Michael W. Groff, MD, Indiana University, Robert F. Heary, MD, UMDNJ, New Jersey Medical School, Mark E. Shaffrey, MD, University of Virginia Health System, pp. 1-24.

* cited by examiner

METHOD AND IMPLANT FOR CONVERTING A TRANSCORPOREAL CORPECTOMY PROCEDURE TO AN INTERVERTEBRAL DISCECTOMY WITH FUSION PROCEDURE

RELATED APPLICATIONS

Not applicable

FEDERALLY SPONSORED RESEARCH OR DEVELOPMENT

Not applicable

TECHNICAL FIELD

The present disclosure relates to a method and implant for operatively converting a transcorporeal procedure to a discectomy and fusion procedure, the method and implant suitable for surgically stabilizing the cervical spine after converting the transcorporeal procedure to a discectomy and fusion procedure.

BACKGROUND

A new surgical method referred to as an intravertebral corpectomy has recently been developed. An intravertebral corpectomy is also sometimes called a transcorporeal procedure or a partial vertebrectomy with endplate preservation. Thus, throughout this disclosure, the terms "intravertebral corpectomy," "transcorporeal" and "partial vertebrectomy," shall be used interchangeably unless otherwise indicated. This disclosed inventive method is a spinal surgical procedure that accesses the anterior aspect of the spinal canal or areas adjacent to or within the spinal canal (the greater spinal canal) from an anterior approach that creates an access channel through a vertebral body of a vertebra of the cervical spine while leaving the vertebral endplates and intervertebral spinal discs generally intact. It is possible to perform this procedure to more than one of the vertebrae of the cervical spine. The intention of this procedure is to leave the intervertebral disc(s) and endplates sufficiently intact in order to allow the discs to perform their normal function as naturally as possible and thereby avoid an intervertebral fusion during surgery for the treatment of a pathology or spinal disorder that requires access to the area behind a cervical vertebral body. Essentially, this procedure allows the surgeon access to the posterior aspect of the vertebral body and access to the anatomy posterior to the vertebral body of the cervical spine.

In certain surgical procedures, a void in the bone of a cervical vertebral body may be created using the transcorporeal approach. During a surgical procedure that includes the creation of a transcorporeal void to the cervical spine, it is possible that factors occur during the surgical procedure that would require the surgeon to intraoperatively abandon the original surgical plan of the transcorporeal procedure, which by definition does not include an intervertebral fusion, and seek an alternative surgical plan which does include an intervertebral fusion.

In other instances, e.g., postoperatively, a patient may have to be taken back to surgery for a surgical revision of the original transcorporeal procedure. This revision may require the inclusion of an intervertebral fusion.

Traditionally, when a surgeon needs to access the posterior aspect of a cervical vertebral body and/or the anterior aspect of the greater spinal canal of the cervical spine of a patient, the surgeon will perform what is known as an Anterior Cervical Discectomy and Fusion (ACDF). Traditionally, ACDF is an approach in which a surgeon first removes a spinal disc between two vertebral bodies in the cervical spine. An alternate procedure called a corpectomy removes two spinal discs and the cervical vertebral body between the discs that are removed. Once these important anatomical structures have been removed, the surgeon has access to the greater spinal canal that was initially without access because of the obstruction of these important anatomical structures, which have now been removed. With the obstructing structures removed, the surgeon can now freely operate on the area that is now exposed, without encumbrance.

Once a surgical procedure has been performed upon the spinal anatomy within the greater spinal canal posterior to the now-removed anatomical structures, other consequences of this surgical practice become evident. The surgeon now has to reconstruct the spine that has had the anatomical structures permanently removed from it. The reconstruction procedure usually includes placing some allograft bone or an artificial device between the remaining vertebrae and screwing a plate onto the adjacent vertebral bodies in order to fuse the surgical site into one mass of bone sufficiently strong enough to support the patient.

In the case of a single disc removal procedure, the surgeon works through the space created between the two vertebrae where the disc was removed. The repair of this void between two adjacent vertebrae that was created by removing one intervertebral disc is commonly referred to as a "one-level procedure" since one disc is removed and the two vertebrae are fused together. When a surgeon removes two intervertebral spinal discs to gain greater access, this procedure is commonly called a "two-level procedure" since two discs are removed. During a two-level procedure, the surgeon may remove the vertebral body between the two spinal discs that have been removed. When two adjacent level discs are removed and the vertebral body between these now-removed discs is also removed, this is commonly called a "two-level procedure with a corpectomy." After performing this two-level discectomy or two-level discectomy with a corpectomy, the spine must be reconstructed. This is typically accomplished using allograft bone and/or synthetic implants and a plate screwed into the bones to hold it all together.

During the transcorporeal procedure, the surgeon gains access to the greater spinal canal by removing at least a portion of the vertebral corpus and creating a pathway through the vertebral body itself instead of removing intervertebral spinal discs for access. The body is able to grow new bone within a vertebral body once bone has been removed, particularly if an appropriate structure is put into place to assist in the healing process. This is in contrast to removing intervertebral discs during traditional ACDF surgery techniques; once spinal discs are removed, they can never grow back or regenerate. By creating a pathway through the vertebral body, which is made up of bone that can be repaired, regrown and healed, the surgeon is able to leave the intervertebral discs generally intact. The transcorporeal procedure gives the surgeon access to the posterior aspect of the vertebral body and the greater spinal canal without the need to terminate the procedure by fusing and stabilizing with implants and hardware one or two levels together into one larger fused bone mass. The result of the transcorporeal procedure is that the patient does not lose motion at these segments by the removal of the intervertebral spinal discs and subsequent fusion.

With the transcorporeal procedure, a substantial portion of the vertebral corpus may be removed while leaving a portion of or all of the vertebral endplates intact. Leaving the endplate or endplates in place and mostly or completely intact results in the intervertebral disc adjacent to the endplate being left in place. This is a great advantage to the patient's recovery and future when the procedure is successful. Currently, a potential outcome of the transcorporeal procedure is that prior to this disclosure, surgeons do not have a suitable alternative if the procedure does not go as planned and an alternate procedure is needed.

During a traditional ACDF where the surgeon removes an intervertebral spinal disc, the disc is replaced, as discussed above, with a piece of allograft or autograft bone or an artificial implant sometimes called an intervertebral spacer. The area is usually secured and held in place by placing a rather large cervical fusion plate that spans over the area where the disc was removed and usually about midway onto the vertebral bodies that are selected to be fused and the plate is screwed into both of the vertebral bodies adjacent to where the disc was removed. The plate is placed approximately midway onto each of the adjacent vertebrae so there is sufficient cancellous bone mass for the screws to engage (purchase). This traditional ACDF technique has been used for years with success and predicable outcomes with the understood primary negative setback being the loss of one motion segment to the patient. Sometimes, a plate-less implant is placed in between the two vertebrae. However, this typically requires screws to be placed through the plate-less implant and into the bones of the adjacent vertebral bodies, therefore still requiring sufficient cancellous bone to be left in place within the adjacent vertebral bodies as similarly would be required by a cervical plate.

In the scenario where two discs are removed along with the vertebral body in between, a longer allograft bone or artificial implant is used, and a longer plate is placed approximately midway onto the adjacent vertebral bodies. Bone screws are screwed into the bony cancellous vertebral corpus with likewise predictable outcomes and success. In the case where two discs are removed along with the vertebral body in between discs, the patient would have the negative setback of the loss of motion at two levels.

In the case of a surgeon who needs to abandon the transcorporeal procedure and convert from the less invasive, less disruptive approach of leaving the disc intact to the more invasive disc removal procedure of an ACDF, a problem arises during the reconstructive phase of the procedure. In this case, when the surgeon prepares to place the plate onto the vertebral body, the surgeon will find that with the vertebral corpus having been previously removed during the now-abandoned transcorporeal approach, there is no anatomical area sufficient to attach the implants including the plate and screws to in the vertebral body since the vertebral body has already been removed. This may require that the surgeon reach out to another adjacent vertebra to find an intact bone mass which will also mean another adjacent potentially healthy disc between the adjacent vertebra being removed only for the purpose of providing an intact anatomical area of an additional vertebra to attach the plate and screws. This will convert a single level cervical fusion into a two-level cervical fusion solely for the purpose of finding enough bone for the implants to properly attach. This will negatively impact the patient as the patient will now lose motion at two disc levels due to an intraoperative surgical need, not because pathology or disease demanded the removal of two discs and motion segments but because the surgeon lacks the method and implants of this disclosure. The present disclosure allows for the conversion of a transcorporeal surgical approach to a single-level anterior cervical discectomy and fusion surgical approach.

The need to convert from an intravertebral corpectomy surgical procedure to a fusion procedure can occur intraoperatively or it can occur post-operatively. When a change occurs intraoperatively, it is often called a conversion, and thus when a surgeon revisits an area postoperatively in another surgery it can be called a revision procedure. For the purpose of clarity in this disclosure, conversion is defined as intraoperatively during the original surgery or during a second revision surgery. The term that can describe either timeline to the procedure is a Converted Intravertebral Corpectomy (or Transcorporeal) Procedure.

The method disclosed herein is contrary to what has been taught throughout the history of cervical spine surgery and the entirety of this method will be counterintuitive to the surgeon. The procedure described herein that will ultimately end up as an anterior cervical discectomy and fusion (ACDF) begins by including the step of removing bone from the vertebral corpus of the vertebral before removing the soft intervertebral disc. This approach contravenes current methodologies.

The history of ACDF teaches that after proper exposure is achieved, the first step of the ACDF procedure is the removal of the intervertebral disc. This is for very clear reasons. When a surgeon is operating upon the anterior aspect of the cervical spine in the performance of an ACDF, the patient is laying on his or her back and the surgeon is working through the front of the spinal column toward the spinal canal and spinal cord. This is delicate surgery and even the most experienced surgeon cannot be casual about this procedure. The intervertebral disc is made up of an outer layer that wraps all the way around the disc and is called the anulus fibrosus. Within this outer layer is the disc material called the nucleus pulposus. The nucleus pulposus is a soft material that is easily grasped and removed. The surgeon can quickly and comfortably work at the removal of the disc material knowing that it is comparatively easy to extract using relatively blunt tipped instruments and behind the last of the inner disc material is the back side of the anulus fibrosus, not to mention the protective posterior longitudinal ligament, adding further protection to the spinal cord. As the surgeon gently removes the soft intervertebral disc, the vertebral body and endplate come into view. As the surgeon finishes removing the disc, the top and bottom endplates of vertebral bodies adjacent to the disc come clearly into view and the surgeon has no remaining questions of where exactly the spinal canal begins and where the spinal cord is.

At this point, with all the anatomy identified, the surgeon knows exactly where he or she is and can begin removing bone with confidence if any bone removal is necessary. Many times, just the removal of the intervertebral disc provides the access to the targeted pathology that the surgeon requires and no significant further dissection is required. At this point, the surgeon may begin the fusion portion of the procedure.

What is therefore needed is an inventive method and implant that provide the surgeon with an alternative, which previously did not exist during instances when the transcorporeal surgical approach needs to be converted to an alternate surgical approach. This is accomplished with this disclosure by reconstructing the void created during the transcorporeal procedure, without unnecessary destruction of adjacent anatomy or unnecessary disruption of healthy anatomy for the purpose of locating an additional point of fixation.

SUMMARY OF THE PRESENT DISCLOSURE

The inventive method and implant disclosed herein allow for a successful conversion from one procedure, the transcorporeal procedure, to a different procedure, the anterior cervical discectomy and fusion procedure, without sacrificing an additional disc level.

The inventive technique disclosed herein initially involves drilling down through the vertebral body of the cervical vertebra, down in the direction toward the spinal canal and spinal cord. This requires a different level of preoperative planning. The surgeon needs to preoperatively determine precisely the distance (depth) of the vertebral body from front to back and drill precisely to that depth and not any more. The instruments required to remove bone are necessarily more aggressive than instruments used to remove soft tissues. Often times these instruments include powered instruments such as drills and high-speed burrs. The surgeon is looking down upon the vertebral body and does not have direct visualization behind the vertebral body as the drill progresses toward the spinal canal and spinal cord. The surgeon must stop the forward progression prior to the drill bit entering the spinal canal.

While drilling into and then through a vertebral body has been done before it has not been done in the order of events covered by the methodology of the present disclosure. Previously, during an anterior cervical discectomy and fusion procedure, when a hole has been drilled into and through the vertebral body, it has been done after the removal of the intervertebral disc has been performed. In actual practice, the technique of drilling a hole all the way through a cervical vertebral body even after the removal of the intervertebral disc is very unpopular because of the uncomfortable aspects of the drilling procedure. There have been techniques taught for devices wherein after removing an intervertebral disc the surgeon drills all the way through a vertebral body in order for a screw for a fixation device such as a cervical plate to be placed in such a manner as to engage both the front wall and posterior wall of a vertebral body. These devices have proven to be widely unpopular and have not found mainstream acceptance even though in these previous procedures, the drilling portion of the procedure is simplified in that it occurs after the intervertebral disc has been removed.

According to one aspect of the invention, a method of converting a transcorporeal procedure into a fusion procedure is provided. The method comprises creating a void in a first vertebral body of a cervical vertebra, the void beginning anteriorly and directed posteriorly creating an exit at a posterior aspect of the vertebral body; removing at least a portion of a cervical intervertebral disc, the disc located between and adjacent to the first vertebral body and a second vertebral body; and performing a fusion procedure between the first vertebral body and the second vertebral body.

In one embodiment of this aspect, the method further comprises inserting an implant such that the implant is affixed to at least a portion of the first vertebral body and at least a portion of the second vertebral body. In another embodiment, at least a portion of the implant occupies the void, fully or partially filling the void. In another embodiment, the method further comprises affixing a second portion of the implant to the second vertebral body. In another embodiment, the method further comprises affixing a cervical plate to the implant.

According to another aspect of the invention, an implantable device for placement into a void in a cervical vertebral body, is provided. The implantable device comprises a first portion that is placed within an abandoned transcorporeal void, the void beginning anteriorly and directed posteriorly creating an exit at a posterior aspect of the vertebral body, the first portion interfacing with a remaining portion of the vertebral body; and a second portion comprising an interface for engagement with a second vertebral body, the second vertebral body adjacent the first vertebral body.

In one embodiment of this aspect, the implantable device comprises a front portion, a rear portion, and at least one side portion, the implantable device having a width of a first length and a height of a second length, where the first length is different second length.

According to another aspect of the invention, a method of placing an implant into an iatrogenically created spinal defect is provided. The method comprises creating a void in a vertebral body of a cervical vertebra, the void beginning anteriorly and directed posteriorly creating an exit at a posterior aspect of the vertebral body; and placing the implant into the void between a superior endplate and an inferior endplate of the vertebra such that the superior endplate and the inferior endplate are not removed; and attaching the implant to an adjacent vertebra.

According to another aspect of the invention, a method of placing an implant into a void in a cervical vertebral body is provided. The method comprises creating a transcorporeal void in at least one vertebra of a cervical spine; removing at least a portion of one endplate of the at least one vertebra; removing at least a portion of the intervertebral disc adjacent to the at least one vertebra; and placing at least one implant within the void so that the implant engages with the at least one vertebra of the cervical spine and at least one adjacent vertebra.

According to another aspect of the invention, a method of attaching a first implant to at least one transcorporeal implant and to at least one adjacent vertebra is provided. The method comprises performing a surgical procedure to a cervical spine, the cervical spine containing the at least one transcorporeal implant; attaching the first implant to the at least one transcorporeal implant; and attaching the first implant to the at least one adjacent vertebra.

According to another aspect of the invention, a method of placing an implant within a cervical spine is provided. The method comprises creating a transcorporeal void in a first cervical vertebral body; altering a form of the transcorporeal void created in the first cervical vertebral body; placing an implant into a space created by the creation and alteration of the transcorporeal void in a first cervical vertebral body, the implant attaching to both the first vertebral body and a second vertebral body of the cervical spine.

According to another aspect of the invention, a method of placing implants within a cervical spine is provided. The method includes attaching a plate to a first transcorporeal implant located in a first cervical vertebral body, and attaching the plate to a second transcorporeal implant located in a second cervical vertebral body.

DETAILED DESCRIPTION OF THE INVENTION

The method and implant of the present disclosure introduce an inventive way of converting from one anterior cervical surgical approach to another anterior cervical surgical approach without unnecessarily sacrificing additional healthy motion segments of the body.

As is well known in the art of spinal surgery, not every patient is the same and patients may have pathologies that vary from patient to patient, and in some cases, it may benefit the patient to have a fusion at one, two, or more levels. The inventive method and implant of the present disclosure anticipates this and can accommodate this need. The inventive method allows a surgeon to only perform the surgical steps that are needed to treat the pathology and avoid unnecessarily removing additional discs, and to avoid fusing levels solely for the purpose of finding a suitable anatomical location for the attachment of the fixation implants. The methods of the present disclosure advantageously utilizes the void created by the abandoned transcorporeal procedure as a point of placement for the implant.

Figure 1:
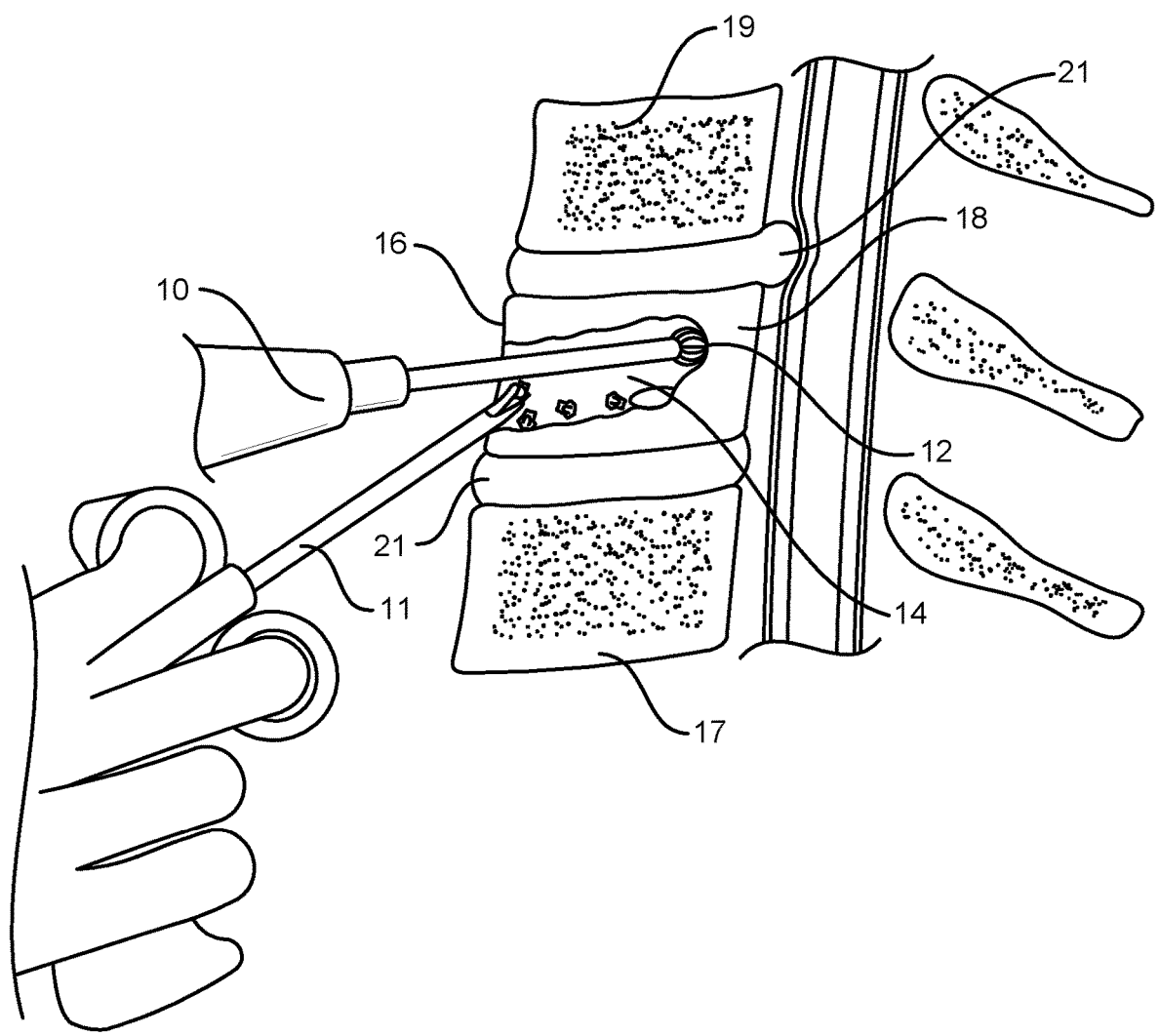
FIG. 1 illustrates the beginning of the creation of a transcorporeal void in accordance with the principles of the present disclosure.
Figure 2:
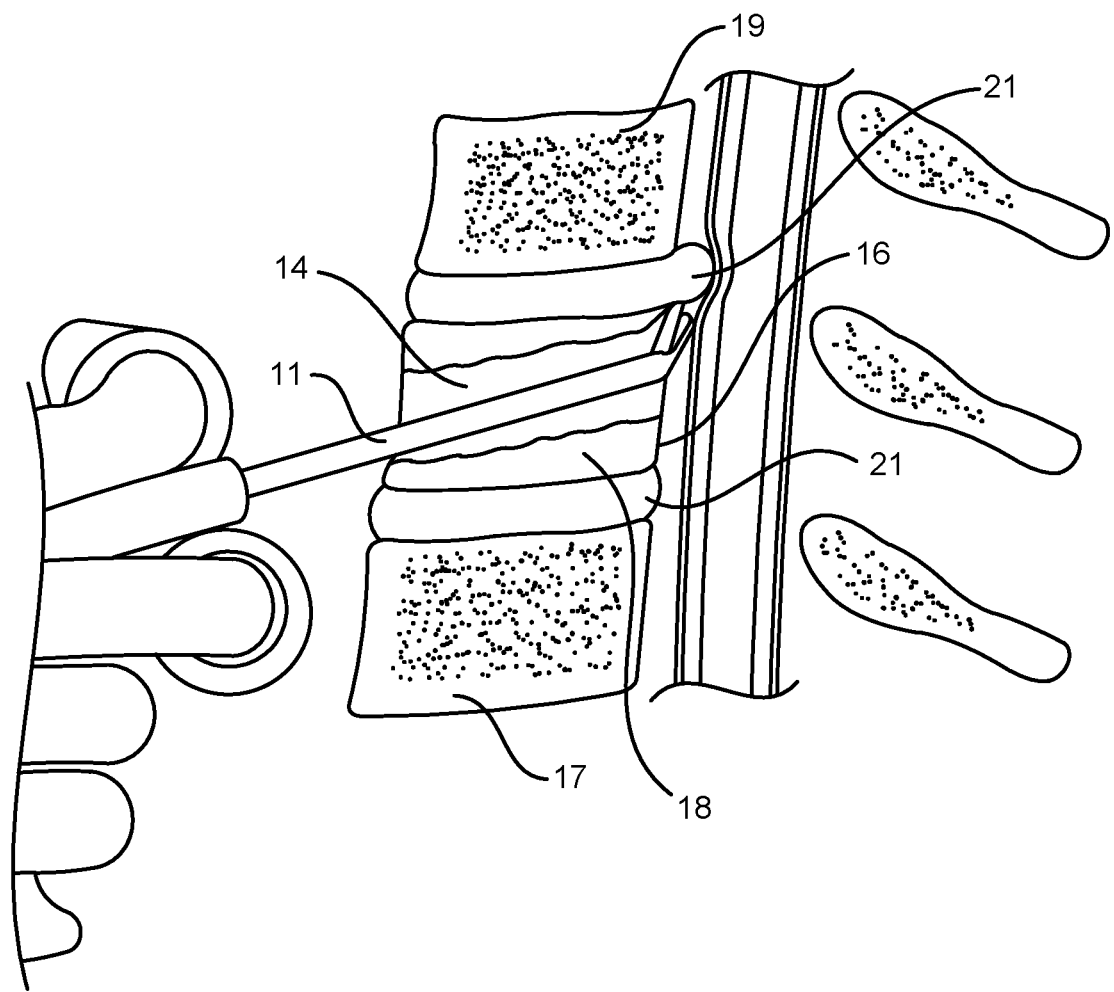
FIG. 2 illustrates the completion of the creation of the transcorporeal void in accordance with the principles of the present disclosure.

Referring now to FIG. 1 and FIG. 2, in accordance with the principles of the present disclosure, a surgeon initiates an transcorporeal procedure by creating a void 14 by removing bone 18 in a first vertebral body 16 of a cervical vertebra between two adjacent vertebrae 17 and 19, the void 14 beginning anteriorly and directed posteriorly creating an exit at a posterior aspect of the vertebral body 16. This could be done, for example, with the use of a dissecting instrument 10 having a burr 12 at its distal end and tool 11. Note disc 21, which resides adjacent to and on either side of the vertebral body 16. After the transcorporeal void 14 is created, the surgeon may then decide, for any number of reasons, to abandon the transcorporeal procedure and convert to an anterior cervical discectomy and fusion procedure. This conversion of procedure is achieved by the incorporation of the methods and implants of the present disclosure, which can perform the roles of intravertebral body replacement, an intervertebral spinal disc replacement, i.e., an intervertebral fusion device, and also provide a point of fixation for the implant by engaging only one additional vertebral body. In one embodiment, the engagement of only one other vertebral body is achieved by having aspects of the spinal implant engage another vertebral body and securely attach to the other vertebral body while also utilizing the void created during the transcorporeal approach as a point of placement and an implant and vertebra connection. This is discussed in further detail below.

Figure 3:
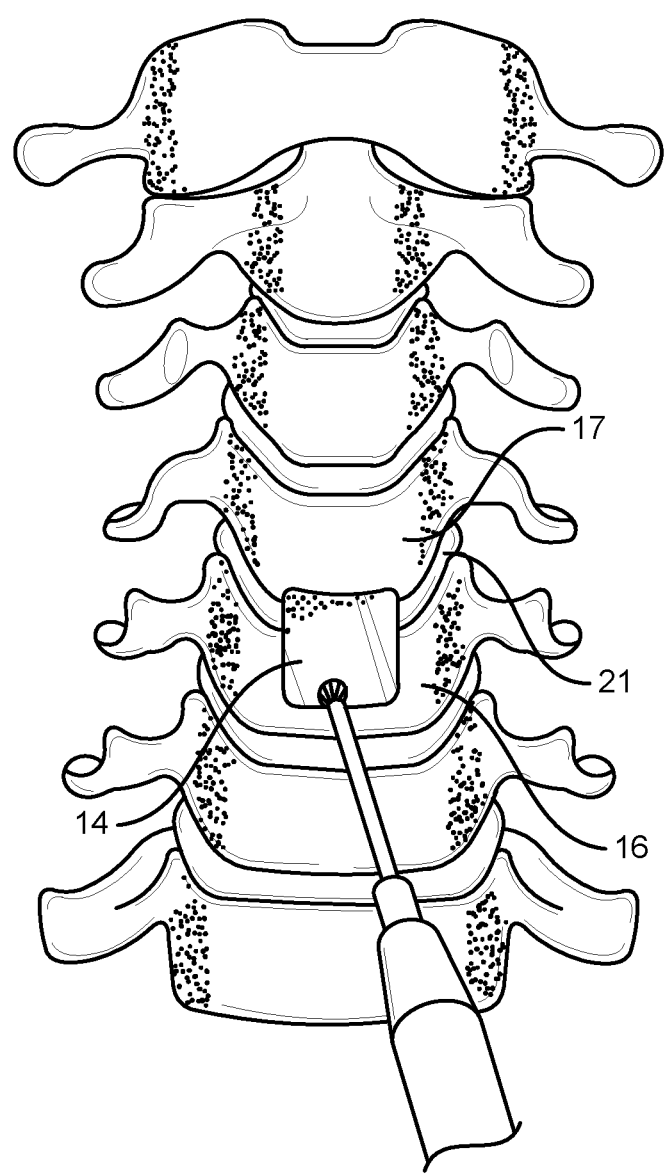
FIG. 3 illustrates the conversion of the transcorporeal void into a fusion procedure in accordance with the principles of the present disclosure.
Figure 4:
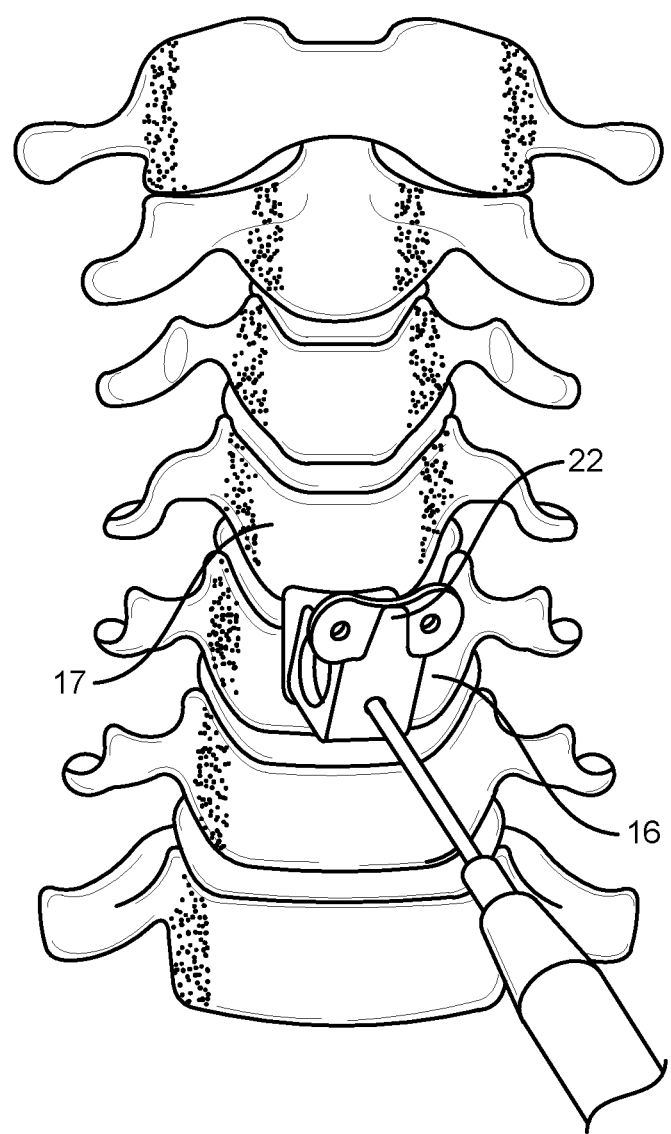
FIG. 4 illustrates the placement of an implant into the converted transcorporeal void where the implant attaches to an adjacent vertebral body in accordance with the principles of the present disclosure.
Figure 5:
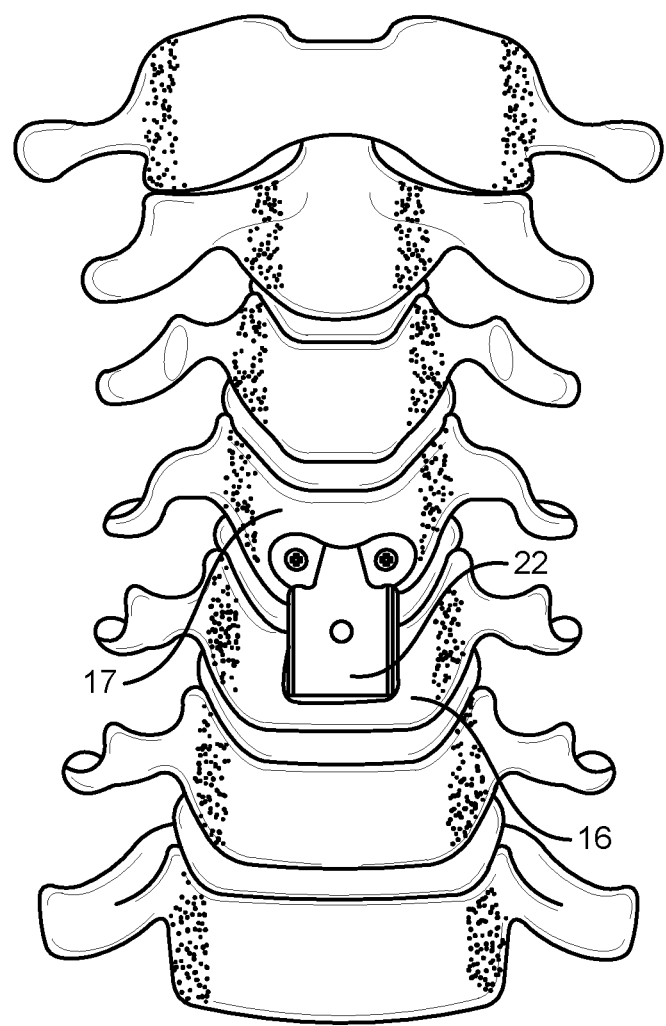
FIG. 5 illustrates an alternate view of the placement of the implant into the converted transcorporeal void where the implant attaches to an adjacent vertebral body in accordance with the principles of the present disclosure.

In accordance with one embodiment of this disclosure, a surgeon may use the void 14 created by the transcorporeal procedure in one vertebral body 16 as a location for placement for an implant that will also be attached to another, adjacent vertebral body. In one example of this use in the course of operating upon a patient, after removing at least a portion of a vertebral body 16 in the course of performing a transcorporeal procedure, the surgeon realizes the need to convert this procedure to an ACDF procedure. This involves attaching the operative vertebral body 16 having the transcorporeal void 14 to an adjacent vertebral body 19 in order to achieve a fusion of the two vertebrae after removing at least a portion of intervertebral disc 21 that lays between the two vertebrae, as shown in FIG. 3. The problem now exists that the traditional anatomy, the mass of the vertebral body that the surgeon would normally use to attach a fusion implant to, such as a cervical plate and screws, is now missing, having been removed during the course of performing the transcorporeal procedure, and described above. Prior to the present disclosure, the surgeon would be required to remove an additional intervertebral disc and involve a third vertebra solely for finding a location to attach a cervical plate or other implant. This present disclosure teaches the utilization of the void 14 created by the transcorporeal procedure as a location for placement for an implant. The implant is affixed to at least a portion of the first vertebral body and at least a portion of a second adjacent vertebral body. This is shown in FIG. 4 and FIG. 5.

In another embodiment of the present disclosure, a method is provided that allows one or more transcorporeal implants 22 to be used as a point of fixation by attaching a cervical fusion plate 23 to the implant 22. Plate 23 need not necessarily be a plate, but might be a rod or bar or any affixation or connection device capable of connecting two implants. This may be performed under a number of different scenarios. One scenario, for example, may occur after one or two transcorporeal procedures has been performed. As an illustrative example of this, in one scenario, transcorporeal procedures have been performed at Cervical Vertebra 5 (C5) and at Cervical Vertebra 6 (C6). This means a bulk of the C5 and C6 vertebrae has been removed and replaced by transcorporeal implants 22 and the disc between these vertebrae has been left in place and is healthy and functional. In this example, these implants 22 may have been in place for some time and the patient has healed and, therefore, each of the implants is solidly and fully integrated with the vertebral body. Removal of these implants 22 would be disruptive to the patient. In this example, after healing, the patient may develop an additional problem at a later time involving the disc between these two vertebrae (C5-C6) or may be an adjacent vertebra (C4-C5). This could occur, for example, by further degeneration or an accident or any other reason. Prior to the present disclosure, the surgeon would be required to attach a fusion plate 23 to adjacent vertebrae in order to find a location for attachment passing over the vertebrae containing the transcorporeal implants 22. Utilizing the methods of the present disclosure, the surgeon is able to avoid unnecessarily involvement of adjacent healthy vertebrae and discs.

Figure 6:
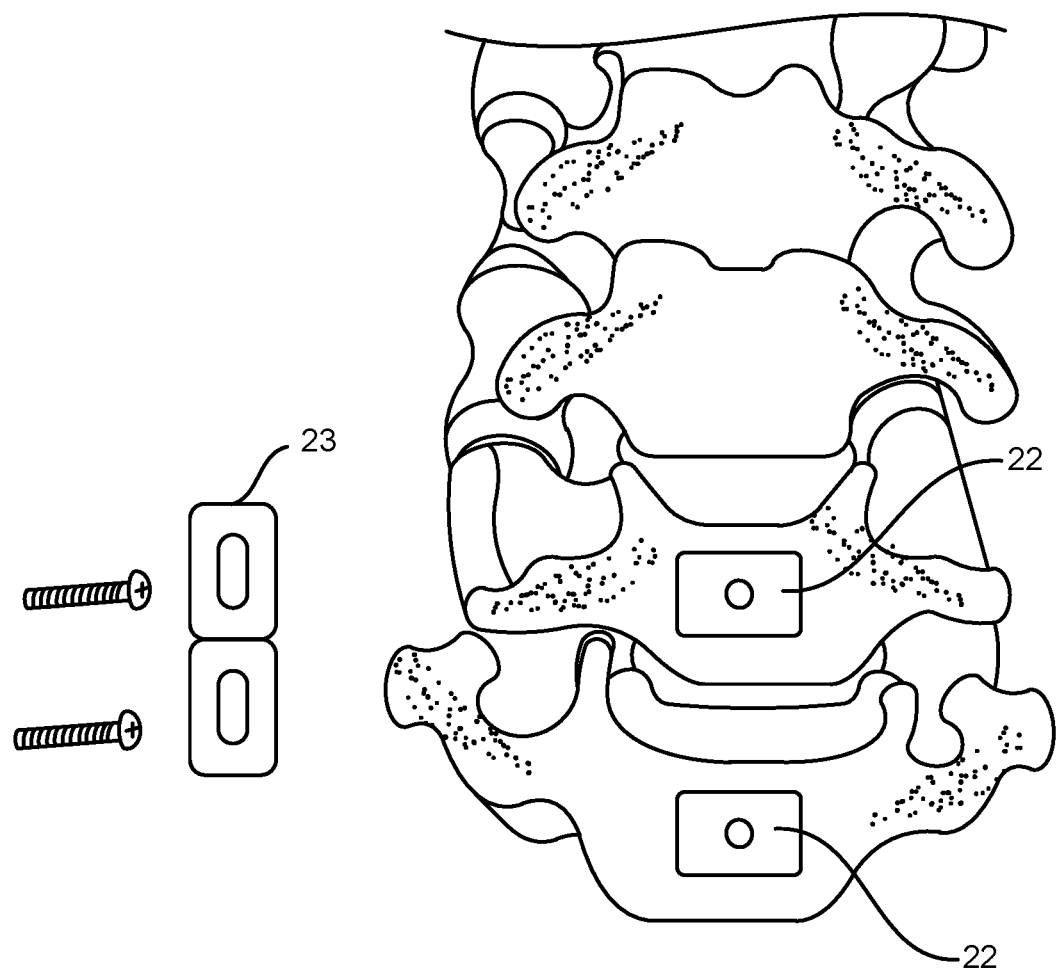
FIG. 6 illustrates the utilization of transcorporeal implants in more than one vertebral body in accordance with the principles of the present disclosure.
Figure 7:
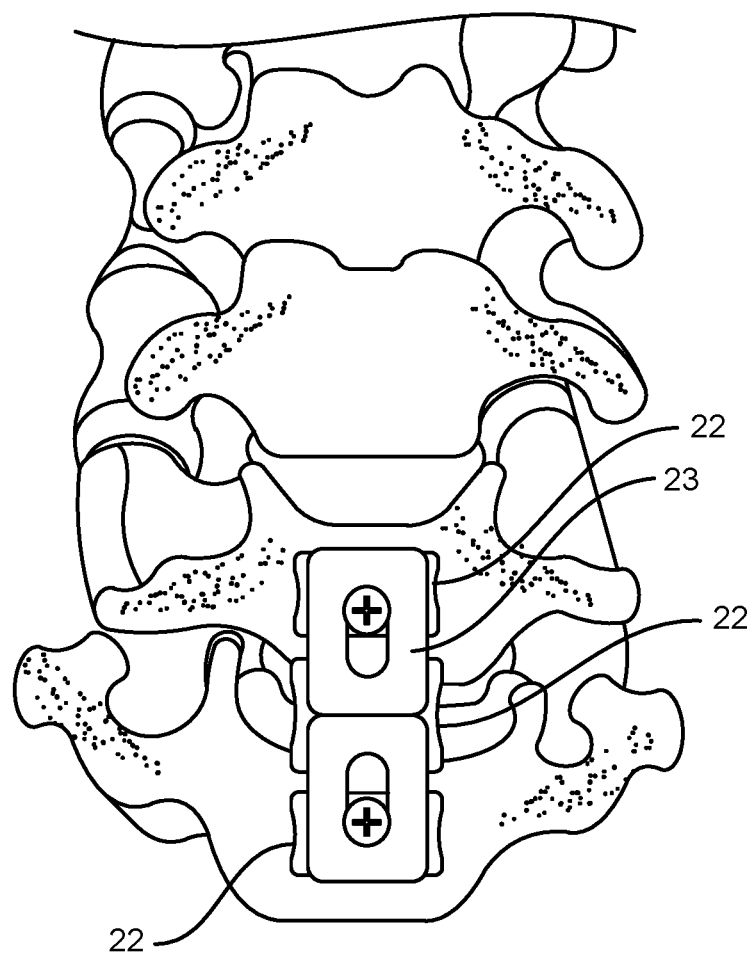
FIG. 7 illustrates the utilization of transcorporeal implants in more than one vertebral body with points of fixation in accordance with the principles of the present disclosure.

Referring now to FIG. 6 and FIG. 7, the features of the design of one embodiment of plate 23 disclosed herein features points of attachment that correspond to the transcorporeal implant 22 or implants that are already in place and securely seated in bone. With the transcorporeal implants 22 securely in place, instead of skipping over them to an adjacent and otherwise unaffected vertebra, fusion plate 23 of the present disclosure directly attaches to the transcorporeal implant 22 or implants that are in place. This means the transcorporeal implants 22 are used as a location for attachment of plate 23 instead of an obstacle to be avoided and bypassed.

In accordance with one embodiment of the method and implant of the present disclosure, the surgeon may attach a plate 23 to a transcorporeal implant 22 that is already in place. An example of this would be if, postoperatively, the intervertebral disc that was not removed using the transcorporeal approach degenerates and needs removal during another surgery. It would be preferred in this case that the surgeon have the ability to attach a unique cervical plate implant onto the transcorporeal implant already in place as opposed to having to remove the transcorporeal implant and having to remove the adjacent healthy disc unnecessarily. In the case of having to remove the disc, with the inventive implant 22 of the present disclosure, the surgeon will be able to remove the disc, place a spinal spacer into the void left by the removed disc, place the plate 23 onto the adjacent vertebral body and the transcorporeal implant 22, and then attach the plate 23 to the transcorporeal implant 22 constituting a first attachment location and attach the plate 23 to a single adjacent vertebral body constituting a second attachment location.

In order to provide the surgeon with appropriate options to treat variations in patient pathology, anatomy and surgical conditions, it should be recognized that during the original surgery, the surgeon may decide to attach a cervical fusion plate 23 to the transcorporeal implant 22 at various times as the surgeon dictates. For these reasons, the present disclosure provides one or more implants 22 either with the cervical fusion plate 23 pre-attached or with the cervical fusion plate 23 ready to be attached by the surgeon during the original surgery or follow up surgeries. It is also within the scope of this disclosure that the surgeon may leave the transcorporeal implant 22 in place, or replace it with a larger one.

Figure 8:
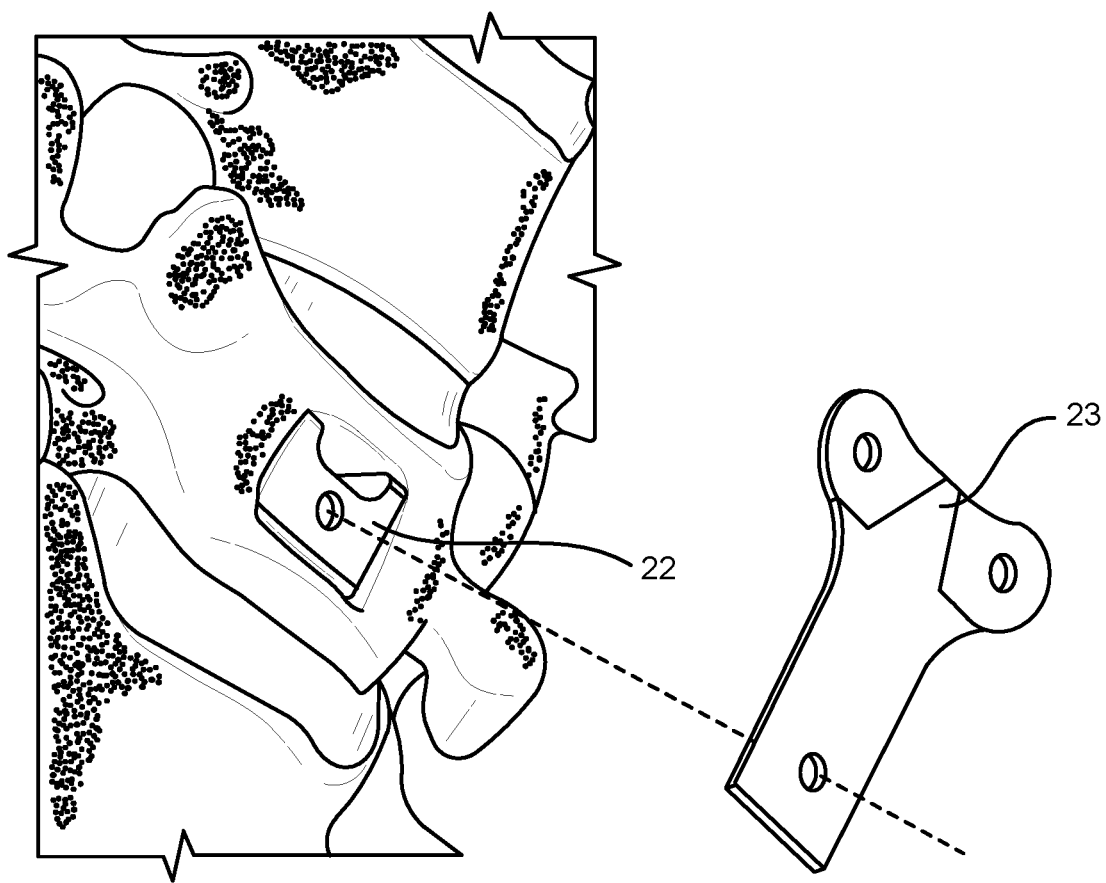
FIG. 8 illustrates a transcorporeal implant placed into one vertebral body as a point of fixation and also showing a plate to be attached to the implant and an adjacent vertebral body.

FIG. 8 illustrates the utilization of a transcorporeal implant 22 in place within a vertebral body and a plate 23 attaching to the implant 22 and one adjacent vertebral body.

Figure 9:
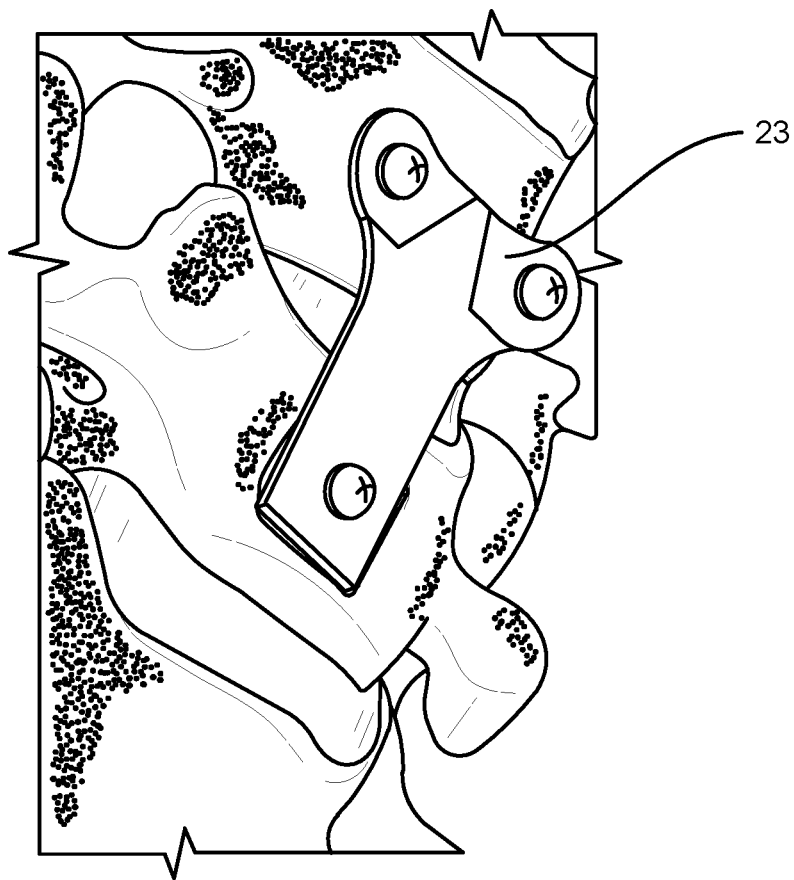
FIG. 9 illustrates a transcorporeal implant placed into one vertebral body as a point of fixation and using an adjacent vertebra as a second point of fixation in accordance with the principles of the present disclosure.

FIG. 9 illustrates transcorporeal implant 22 placed into one vertebral body as a point of fixation and using plate 23 and an adjacent vertebra to provide a second point of fixation.

As discussed herein, during the transcorporeal procedure, the surgeon gains access to the greater spinal canal by removing at least a portion of the vertebral corpus, creating a pathway through the vertebral body itself instead of removing intervertebral spinal discs for access. This is in distinct contrast to removing an intervertebral disc or discs as performed during traditional ACDF surgery techniques that permanently remove spinal discs, which once removed. never grow back or regenerate. By creating a pathway through the vertebral body, which is made up of bone that can be repaired, regrown and healed, the surgeon is able to leave the intervertebral discs generally intact.

As is understood by one skilled in the art of spinal surgery, not every surgery goes according to plan. There is a wide range of reasons during virtually any type of surgery wherein the surgical plan needs to take a different direction. Currently when a surgeon intraoperatively abandons a transcorporeal surgical procedure being performed in the cervical spine, the typical solution, due to the removal of bone that has been performed upon a first vertebral body, is to remove the entirety of the first vertebral body thus performing a full corpectomy which necessarily requires the removal of the two adjacent intervertebral discs. The performing of a full corpectomy requires the inclusion of three vertebrae. The first vertebra in which the transcorporeal void was created and that has been abandoned leaving no room for implant attachment, and an adjacent second and third vertebrae for the attachment of implants and fusion devices. As described by this disclosure, the inventive technique and implant allows for a change in the original surgical plan by first creating a transcorporeal void in a first cervical vertebral body, altering a form of the transcorporeal void created in the first vertebral body by removing at least a portion of the cervical intervertebral disc and performing a fusion procedure between the first and second vertebral bodies and placing an implant into a space created in the first cervical vertebral body and/or into a space created by removal of the intervertebral disc. The implant can then be attached to both the first vertebral body and a second vertebral body of the cervical spine.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

We claim:

1. A method of performing an anterior cervical fusion procedure, the method comprising:
   creating a void in a first vertebral body of a cervical vertebra, the void beginning anteriorly and directed posteriorly creating an exit at a posterior aspect of the vertebral body;
   after the creation of the void in the first vertebral body, removing at least a portion of a cervical intervertebral disc, the disc located adjacent to the first vertebral body and between the first vertebral body and a second vertebral body; and
   performing a fusion procedure between the first vertebral body and the second vertebral body.

2. The method of claim 1, further comprising inserting an implant such that the implant is affixed to at least a portion of the first vertebral body and at least a portion of the second vertebral body.

3. The method of claim 2, wherein at least a portion of the implant occupies the void.

4. The method of claim 2, further comprising affixing a second portion of the implant to the second vertebral body.

* * * * *